United States Patent [19]
Lynn

[11] Patent Number: 5,924,597
[45] Date of Patent: Jul. 20, 1999

[54] BUILDING FRAGRANCE DISTRIBUTION SYSTEM AND METHOD

[76] Inventor: David M. Lynn, 401 Craver Rd., Welcome, N.C. 27374

[21] Appl. No.: 08/933,352

[22] Filed: Sep. 19, 1997

[51] Int. Cl.[6] .......................................................... B67B 7/00
[52] U.S. Cl. .............................. 222/1; 222/645; 222/504; 422/124
[58] Field of Search ................................. 222/1, 642, 645, 222/646, 647, 648, 504; 422/124; 261/DIG. 15, DIG. 17

[56] References Cited

U.S. PATENT DOCUMENTS

| | | | |
|---|---|---|---|
| 2,686,944 | 8/1954 | Gubelin | 222/647 |
| 3,993,444 | 11/1976 | Brown | 261/DIG. 17 |
| 4,603,030 | 7/1986 | McCarthy | 422/4 |
| 4,629,604 | 12/1986 | Spector | 422/124 |
| 4,631,387 | 12/1986 | Glucksman | 219/272 |
| 4,645,353 | 2/1987 | Kavoussi et al. | 368/12 |
| 5,011,632 | 4/1991 | Yano et al. | 261/81 |
| 5,029,729 | 7/1991 | Madsen et al. | 222/1 |
| 5,111,477 | 5/1992 | Muderlak | 392/390 |
| 5,174,967 | 12/1992 | Fukuhara | 422/124 |
| 5,175,791 | 12/1992 | Muderlak et al. | 392/390 |

OTHER PUBLICATIONS

Entire instruction sheet for ALTRONIX® Corporation PT–724 Digital Programmable Timer, revised Feb. 1995.
Entire instruction sheet for ALTRONIX® Corporation 6030 Multi–Purpose Timer, revised Feb. 1995.
Entire instruction sheet for Model DSL–300 Digital Thermostat (undated).

*Primary Examiner*—Gregory L. Huson

[57] ABSTRACT

A fragrance dispensing apparatus and method is disclosed for use in a multi-room building having an existing HVAC system ventilated by a forcing fan. The apparatus includes a plurality of fragrance containers, a plurality of solenoids, a plurality of programmable timers, and a single fan timer. A fragrance container is mounted in communication with the HVAC ductwork leading into a given room. Each fragrance container is controlled by a separate solenoid, which is in turn controlled by a separate programmable timer. All of the programmable timers are connected to a single fan timer, which controls the operation of the forcing fan. The method allows one or more of the programmable timers to activate corresponding containers to dispense fragrances as the forcing fan runs to distribute the fragrances into the rooms supplied by the ductwork.

7 Claims, 2 Drawing Sheets

BUILDING FRAGRANCE DISTRIBUTION SYSTEM AND METHOD

BACKGROUND OF THE INVENTION

1. Field Of The Invention

The invention pertains generally to the field of fragrance distribution inside buildings, and pertains specifically to dispensing selected types and quantities of fragrances into the existing heating-ventilation-air-conditioning (HVAC) ductwork that supplies air to different rooms within the building.

2. Description Of Related Art And Objectives Of The Invention

Building dwellers are concerned with the quality of the ambient indoor air. Offensive odors affect the quality of indoor air, and the art has provided several devices and methods for masking those odors. Some such devices are hand held and must be manually operated, thus drawing human resources away from other tasks. In other indoor situations, it is simply desirable to improve the surroundings by dispensing selected fragrances at selected times. Such dispensing devices are preferably automated so that they will operate without active human intervention.

The art has provided several fragrance dispensing systems such as U.S. Pat. No. 5,011,632 which discloses a fragrance generation apparatus that dispenses selected amounts of fragrance at selected time intervals into the air inside buildings. U.S. Pat. No. 4,603,030 discloses a programmable scent-emitting system for dispensing a plurality of fragrances as does U.S. Pat. No. 4,629,604. U.S. Pat. No. 4,631,387 discloses an aroma generating apparatus while U.S. Pat. No. 4,645,353 discloses an alarm clock designed to emit a scent, rather than a noise or a light, at a selected time. U.S. Pat. Nos. 5,111,477 and 5,175,791 disclose electrically-operated fragrance diffusers. However, none of these patents disclose a device or method which provides the needed versatility and capability desirable today.

The shortcomings in conventional devices and methods motivated the instant invention, and a first objective is to provide an apparatus for dispensing fragrance into HVAC ductwork ventilated by a forcing fan, the apparatus comprising a plurality of fragrance containers joined to a plurality of programmable timers, each of the programmable timers for selectively operating one of said containers, each of the fragrance containers for dispensing fragrance into the HVAC ductwork supplying a different room.

Another objective is to provide a fragrance dispensing apparatus comprising a plurality of solenoids, one each of said solenoids joined to one of the fragrance containers for selectively dispensing a fragrance from the container into the HVAC ductwork.

Still another objective is to provide a method for using a fragrance dispensing apparatus which comprises a programmable timer that allows the fragrance to be dispensed into the HVAC ductwork at selected times and for selected durations.

A further objective is to provide a fragrance dispensing system that comprises a fan timer that operates the forcing fan for a selected duration after the fragrance is dispensed into the HVAC ductwork, thereby distributing the fragrance into the room supplied by the ductwork.

Various other objectives and advantages of the present invention will become apparent to those skilled in the art as a more detailed description is set forth below.

SUMMARY OF THE INVENTION

The aforementioned objectives are realized by the instant invention which discloses a fragrance dispensing apparatus and method which uses HVAC ductwork ventilated by a forcing fan. The apparatus comprises one or more fragrance containers, each one of the containers being mounted in communication with the ductwork leading into a given room. The several containers may store similar or dissimilar fragrances, depending on the desires of the user. Each of the various containers includes a dispenser such as a spray nozzle, for releasing the fragrance from the container into the ductwork. Each of these dispensers is joined to an actuator, such as a solenoid, for activating the dispenser. Each of these actuators is joined to a separate programmable timer, which selectively operates the solenoid at programmed times and durations to dispense fragrance from a given container into the ductwork. All of the programmable timers are connected to a single fan timer, which controls the operation of the forcing fan. The method of use allows any one programmable timer to cause a fragrance container to dispense fragrance into the ductwork, while the fan timer activates the forcing fan to distribute the fragrance from the ductwork into the designated room.

BRIEF DESCRIPTION OF THE DRAWINGS

FIG. 3 is a schematic view of the fragrance container and the dispensing apparatus thereof.

DESCRIPTION OF THE PREFERRED EMBODIMENTS

The preferred embodiment of the apparatus of the invention comprises a plurality of fragrance containers located in fluid communication with existing building HVAC ductwork and provides conventional household pressurized aerosol containers with suitable fragrances. Each of the containers includes a means for dispensing the fragrance from the can, preferably a conventional spray nozzle mounted atop the container. Each of the dispensing means is also joined to separate means for activating the dispensing means which are preferably conventional solenoids. Each of the solenoids is connected to a separate programmable timer, preferably an ALTRONIX® PT-724 Digital Programmable Timer. All of the programmable timers are connected to a single fan timer, preferably an ALTRONIX® 6030 Multi-Purpose Timer. The fan timer is connected to a standard forcing fan that drives air through the ductwork and ventilates the building.

The preferred method allows the user to program the PT-724 timers to dispense the fragrance at specified, selected times for selected rooms and for selected durations.

DETAILED DESCRIPTION OF THE DRAWINGS AND OPERATION OF THE INVENTION

Figure 1:
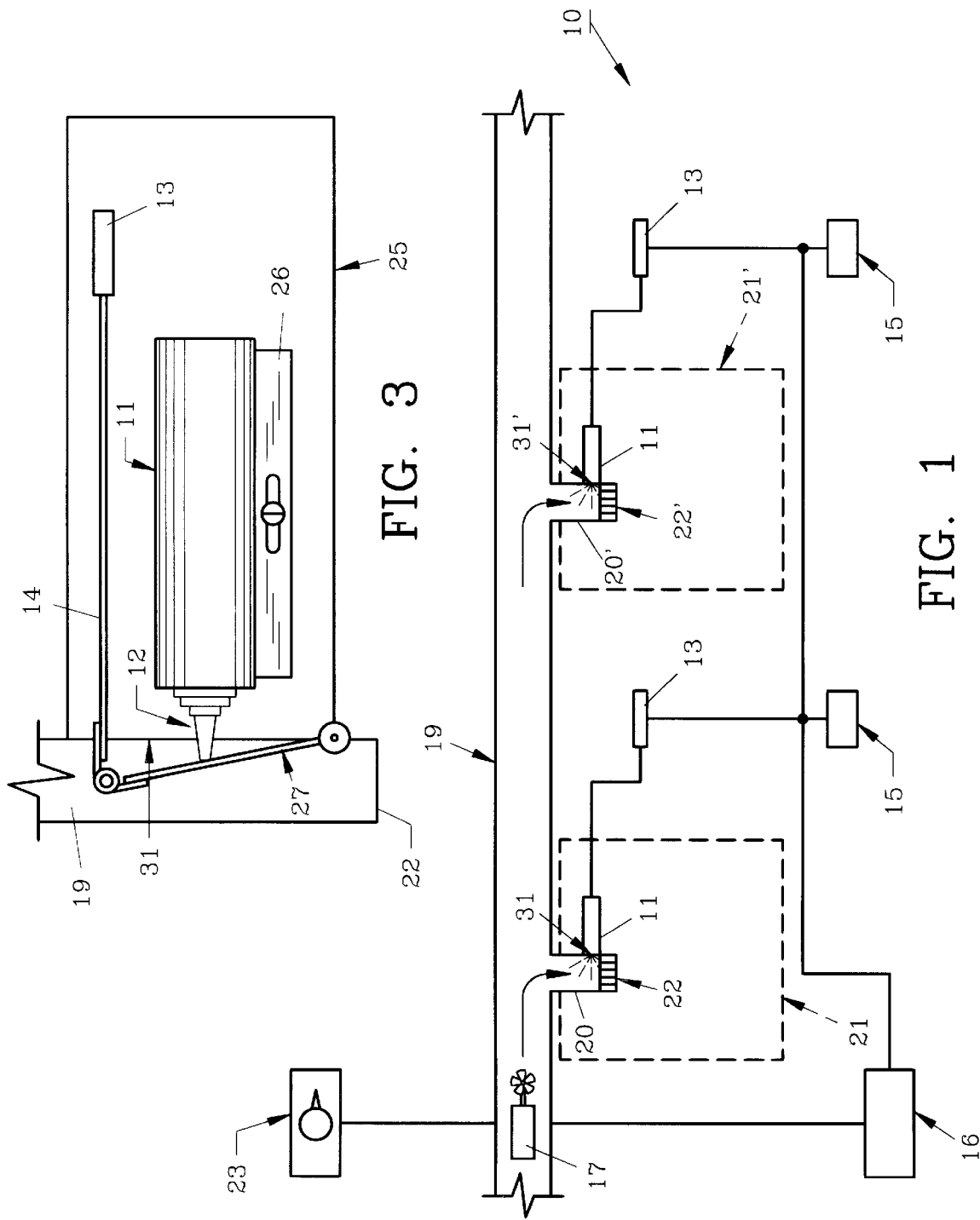
FIG. 1 is a schematic view of the preferred embodiment of the invention shown in its operating environment connected to HVAC ductwork.

For a better understanding of the invention, turning now to the drawings, FIG. 1 shows a schematic of the preferred embodiment, fragrance dispensing apparatus 10, shown in its operating environment joined to ductwork 19. Ductwork 19 includes a plurality of branches 20, 20' each of which feed different rooms 21, 21' respectively with air. Although only two branches 20, 20' and two rooms 21, 21' are illustrated, ductwork 19 could feed any number of branches and rooms as desired. Each branch 20, 21' terminates with a register 22, 22' which admits air into rooms 21, 21'. Located proximate to registers 22, 22' are apertures 31, 31' allowing container 11 to communicate with ductwork 19. Ductwork 19 is ventilated by forcing fan 17, which drives air through branches 20, 20' and into rooms 21, 21'. Forcing fan 17 is connected to, and regulated by, thermostat 23. Thermostat 23 typically includes four output electrical control signals: one signal to control the heating apparatus, one signal to control the cooling apparatus, one common reference signal, and one signal to control forcing fan 17.

Fragrance dispensing apparatus 10 comprises a plurality of containers 11, a plurality of solenoids 13, a plurality of programmable timers 15, fan timer 16, and thermostat 23. Each container 11 is mounted in communication with a given branch 20 feeding a given room 21, and is preferably mounted near register 22. Container 11 stores a selected fragrance, and is mechanically joined to a separate solenoid 13. Solenoid 13 causes container 11 to selectively dispense fragrance into branch 20. Each solenoid 13 is electrically connected to a separate programmable timer 15. Thus, for each branch 20 receiving fragrance, there will be at least one container 11, at least one solenoid 13, and at least one programmable timer 15. All programmable timers 15 are electrically connected to a single fan timer 16. Fan timer 16 is electrically connected to forcing fan 17. When a given programmable timer 15 activates, then fan timer 16 immediately activates, causing forcing fan 17 to run. Forcing fan 17 then distributes fragrance from branch 20 into room 21.

Programmable timer 15 is preferably a PT-724 Digital Programmable Timer as manufactured by ALTRONIX Corporation of Brooklyn, N.Y. As described in the PT-724 Instruction Sheet, the contents of which are hereby incorporated by reference, the PT-724 includes in pertinent part an LCD display, a keypad, a relay, and a clock. The display and keypad allow the user to set the clock and to program events into the PT-724, and the relay implements the programmed events. By programming events, the user can order the relay to energize or de-energize at selected times, or to pulse (remain energized) at a selected time for a selected duration. The PT-724 also allows the user to modify or cancel selected events, or to erase all events. By programming events into the PT-724, the user can control when fragrance is dispensed into a given room.

Fan timer 16 is preferably a 6030 Multi-Purpose Timer, also manufactured by ALTRONIX Corporation of Brooklyn, N.Y. As described in the 6030 Instruction Sheet, the contents of which are hereby incorporated by reference, the 6030 essentially provides a timed interval having a duration selected by the user. At the end of this timed interval, a relay is energized, and forcing fan 17 runs. By adjusting the time interval on the 6030, the user can control how long forcing fan 17 runs after a fragrance is dispensed into a given room (21).

Figure 2:
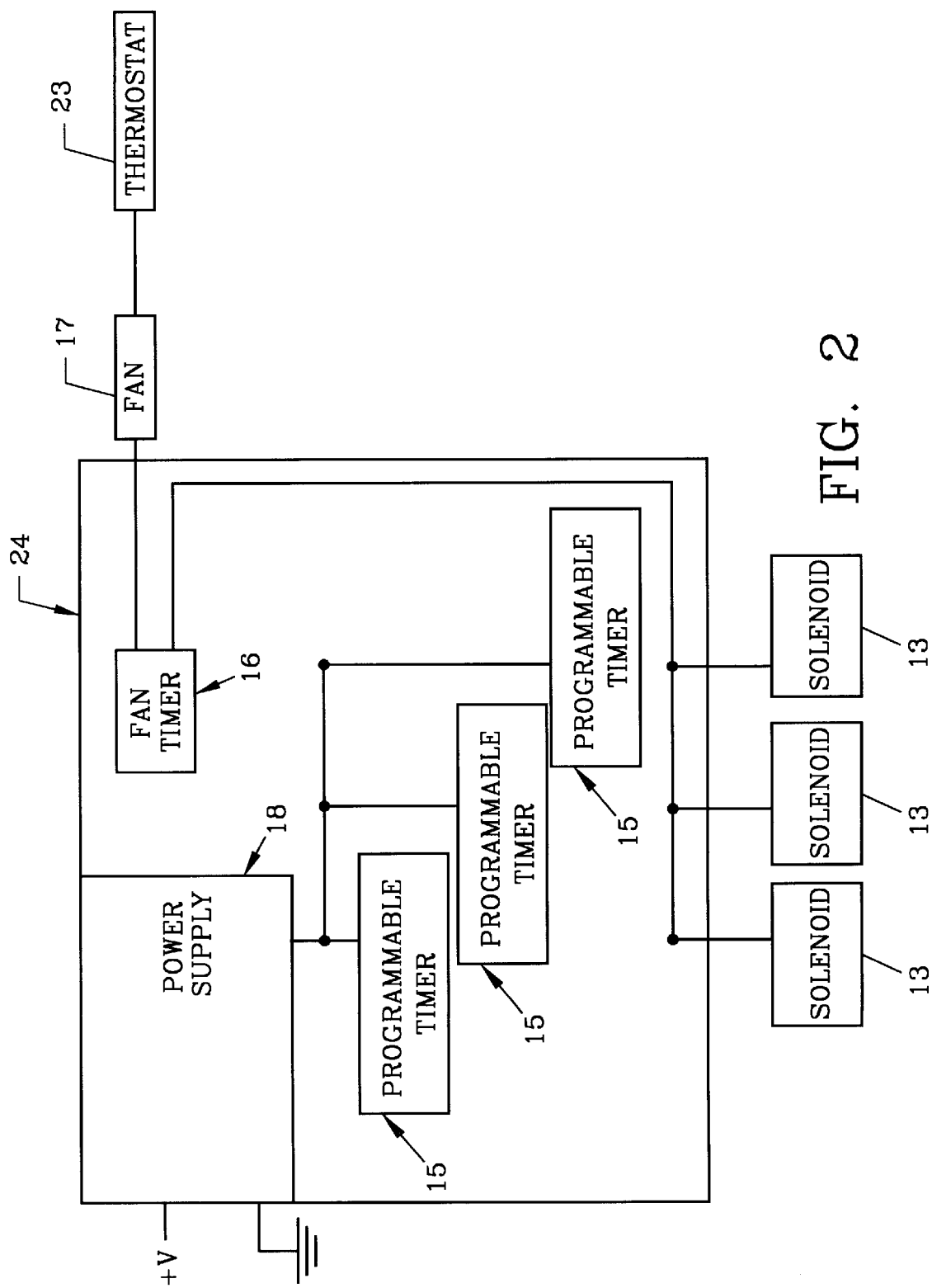
FIG. 2 is a schematic view of the preferred embodiment shown isolated from the HVAC ductwork.

FIG. 2 is an electrical schematic of the preferred embodiment, fragrance dispensing apparatus 10, and is shown isolated from its operating environment. Main housing 24 encloses power supply 18, a plurality of programmable timers 15, and fan timer 16. Power supply 18 is conventional and converts input 120 volt AC current into output low-voltage (12–24 volts) current for programmable timers 15 and fan timer 16. A rechargeable backup battery (not shown) might be included to supply power should the 120 volt supply fail or suffer interruption. The plurality of programmable timers 15 are each connected to a single fan timer 16. Each programmable timer 15 is connected to a separate solenoid 13, which is located remotely from main housing 24. Fan timer 16 is connected to and regulates forcing fan 17, which is also located remotely from main housing 24.

Forcing fan 17 is also regulated by thermostat 23. Preferably, output from fan timer 16 is connected to forcing fan 17 in parallel with the aforementioned output signal from thermostat 23 that controls forcing fan 17.

FIG. 3 is a schematic of fragrance container 11 mounted in communication with branch 20 of ductwork 19 as seen in FIG. 1. Remote housing 25 encloses container 11, solenoid 13, bracket 26, linkage 14, and lever 27. Fragrance container 11 includes nozzle 12, which provides means for dispensing fragrance from container 11. Nozzle 12 is preferably operated by depressing it axially toward container 11. Lever 27 is pivotally joined to remote housing 25, and is positioned so that it is contiguous with nozzle 12 when solenoid 13 is not energized. Linkage 14 connects lever 27 to solenoid 13 so when solenoid 13 is energized, linkage 14 draws lever 27 against nozzle 12 to dispense or spray fragrance from container 11. The sprayed fragrance enters ductwork 19, preferably through an aperture 31 provided in ductwork 19, proximate nozzle 12 (see FIG. 1). Bracket 26 is joined to remote housing 25 and holds container 11 securely in place. Bracket 26 is preferably adjustable along its longitudinal axis to accommodate fragrance containers 11 having different lengths.

The method of using fragrance dispensing apparatus 10 is as follows. The user, such as a homeowner, first decides when fragrances are to be dispensed into which rooms. The user then programs each programmable timer 15 for a given room 21, 21' to dispense fragrance at the selected time and duration. If programmable timer 15 is implemented with PT-724, the user has two options. First, the user can program an initial event wherein the relay energizes to release fragrance and then a subsequent event wherein the relay de-energizes to cease releasing fragrance. Second, the user can program a pulse event wherein the relay remains energized only for a selected duration, thus releasing fragrance only during that duration.

When it is time for a programmed event, programmable timer 15 energizes its relay (not shown), which in turn energizes solenoid 13. When solenoid 13 is energized, it activates nozzle 12 on container 11 to dispense fragrance into, for example, branch 20. When programmable timer 15 energizes its relay, fan timer 16 immediately initiates its timing cycle, thus causing forcing fan 17 to run, thereby distributing the fragrance from branch 20 into room 21 (see FIG. 1).

As described above, fragrance dispensing apparatus 10 preferably comprises a plurality of containers 11 mounted in a plurality of rooms 21. Thus, the user can have different fragrances dispensed into different rooms at different times by programming the several programmable timers 15 appropriately. Apparatus 10 also allows fragrances to be dispensed into multiple rooms simultaneously, owing to the connection of all programmable timers 15 with a single fan timer 16. Several alternative embodiments are anticipated, such as the placement of all fragrance containers for spraying into ductwork 19, as opposed to spraying into separate branches 20, 20' as aforedescribed.

Thus, the illustrations and examples provided herein are for explanatory purposes and are not intended to limit the scope of the appended claims as various modifications and configurations may be implemented by those skilled in the art.

I claim:

1. A system for dispensing fragrances throughout the interior of a building, said system comprising:

a) ductwork;

b) a plurality of fragrance containers, said fragrance containers being in fluid communication at different points along said ductwork;
c) a plurality of means for dispensing fragrance from said containers into said ductwork, each of said plurality of dispensing means attached to different ones of said plurality of containers;
d) a plurality of means for activating each of said plurality of dispensing means, each of said plurality of activating means connected to different ones of said plurality of dispensing means, said activating means for selectively operating each of said dispensing means;
e) a plurality of programmable timers, each of said timers in electrical communication with different ones of said plurality of activating means;
f) a forcing fan, said forcing fan positioned in said ductwork; and
g) a fan timer, said fan timer in electrical communication with each of said programmable timers and with said forcing fan, said fan timer for controlling said forcing fan.

2. The system of claim 1 wherein each of said fragrance containers comprising a pressurized can.

3. The system of claim 2 wherein each of said dispensing means comprising an aerosol spray nozzle.

4. The system of claim 3 wherein each of said activating means comprising a solenoid.

5. The system of claim 4 wherein each of said programmable timers for energizing different ones of said activating means, each of said programmable timers comprising means for energizing said solenoids and means for de-energizing said solenoids to cease dispensing fragrance from said container.

6. A method of dispensing scent throughout the interior of a building, said method comprising the steps of:
a) attaching a fragrance system to ductwork, said system comprising:
   i) a plurality of fragrance containers, said fragrance containers being in fluid communication at different points along said ductwork;
   ii) a plurality of means for dispensing fragrance from said containers into said ductwork, each of said plurality of dispensing means attached to different ones of said plurality of containers;
   iii) a plurality of means for activating each of said plurality of dispensing means, each of said plurality of activating means connected to different ones of said plurality of dispensing means, said activating means for selectively operating each of said dispensing means;
   iv) a plurality of programmable timers, each of said timers in electrical communication with different ones of said plurality of activating means;
   v) a forcing fan, said forcing fan positioned in said ductwork; and
   vi) a fan timer, said fan timer in electrical communication with each of said programmable timers and with said forcing fan, said fan timer for controlling said forcing fan; and
b) selectively dispensing different fragrances into different rooms with said system.

7. The method of claim 6 wherein dispensing different fragrances comprises the step of dispensing different fragrances simultaneously.

* * * * *